(12) United States Patent
Ladet et al.

(10) Patent No.: US 8,512,728 B2
(45) Date of Patent: Aug. 20, 2013

(54) METHOD OF FORMING A MEDICAL DEVICE ON BIOLOGICAL TISSUE

(75) Inventors: Sebastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 611 days.

(21) Appl. No.: 12/708,798

(22) Filed: Feb. 19, 2010

(65) Prior Publication Data

US 2010/0217287 A1 Aug. 26, 2010

Related U.S. Application Data

(60) Provisional application No. 61/154,372, filed on Feb. 21, 2009.

(51) Int. Cl.
| | |
|---|---|
| *A61F 13/00* | (2006.01) |
| *C12N 11/08* | (2006.01) |
| *C12N 11/06* | (2006.01) |
| *C07K 17/08* | (2006.01) |
| *C07K 17/06* | (2006.01) |

(52) U.S. Cl.
USPC ........ 424/422; 424/443; 435/180; 435/181; 530/402; 530/815; 530/816

(58) Field of Classification Search
None
See application file for complete search history.

(56) References Cited

U.S. PATENT DOCUMENTS

| | | | |
|---|---|---|---|
| 3,767,085 A | 10/1973 | Cannon et al. | |
| 4,359,049 A | 11/1982 | Redl et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 5,328,840 A * | 7/1994 | Coller | 435/7.25 |
| 5,372,585 A | 12/1994 | Tiefenbrun et al. | |
| 5,538,781 A * | 7/1996 | Rao et al. | 442/217 |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,911,942 A | 6/1999 | Fofonoff et al. | |
| 6,107,365 A | 8/2000 | Bertozzi et al. | |
| 6,107,453 A | 8/2000 | Zuccato et al. | |
| 6,267,957 B1 * | 7/2001 | Green et al. | 424/94.5 |
| 6,451,032 B1 | 9/2002 | Ory et al. | |
| 6,534,611 B1 | 3/2003 | Darling et al. | |
| 6,552,103 B1 | 4/2003 | Bertozzi et al. | |
| 6,570,040 B2 | 5/2003 | Saxon et al. | |
| 6,576,000 B2 | 6/2003 | Carrison | |
| 6,881,766 B2 | 4/2005 | Hain | |
| 7,012,126 B2 | 3/2006 | Matsuda et al. | |
| 7,044,982 B2 * | 5/2006 | Milbocker | 623/23.72 |
| 7,105,629 B2 | 9/2006 | Matsuda et al. | |
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,534,431 B2 * | 5/2009 | McBride et al. | 424/136.1 |
| 7,618,944 B2 | 11/2009 | Breitenkamp et al. | |
| 7,650,588 B2 | 1/2010 | Ivansen | |
| 7,667,012 B2 | 2/2010 | Saxon et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0094237 A1 * | 5/2003 | Ogle et al. | 156/330 |
| 2003/0100086 A1 | 5/2003 | Yao et al. | |
| 2003/0135238 A1 | 7/2003 | Milbocker | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2005/0038472 A1 | 2/2005 | Furst | |
| 2005/0148032 A1 | 7/2005 | Saxon et al. | |
| 2005/0222427 A1 | 10/2005 | Sharpless et al. | |
| 2005/0233389 A1 | 10/2005 | Ting et al. | |
| 2005/0272662 A1 * | 12/2005 | Stupp et al. | 514/17 |
| 2006/0018948 A1 | 1/2006 | Guire et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0147963 A1 | 7/2006 | Barone et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0020620 A1 | 1/2007 | Finn et al. | |

(Continued)

FOREIGN PATENT DOCUMENTS

| | | |
|---|---|---|
| EP | 0077098 A2 | 4/1983 |
| EP | 0328050 A2 | 8/1989 |

(Continued)

OTHER PUBLICATIONS

Q. Shi, et al., "The Immobilization of Proteins on Biodegradeable Polymer Fibers via Click Chemistry", Biomaterials, 29, (2008), pp. 1118-1126.

(Continued)

*Primary Examiner* — David M Naff

(57) ABSTRACT

A method for in situ formation of a medical device on biological tissue includes attaching a plurality of reactive members of a primary specific binding pair to a surface of the biological tissue, and providing a plurality of fibers having attached thereto a plurality of complementary reactive members of the primary specific binding pair, wherein upon contact of the reactive members on the surface of the biological tissue with the complimentary reactive members on the fibers, covalent bonds are formed between the reactive members and the complementary reactive members, thus adhering the fibers to the tissue. The fibers can incorporate functionalities which may cause them to bind to one another.

33 Claims, No Drawings

(56) References Cited

U.S. PATENT DOCUMENTS

| | | |
|---|---|---|
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2009/0012457 A1 | 1/2009 | Childers et al. |
| 2009/0018646 A1 | 1/2009 | Zhao |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0121022 A1 | 5/2010 | Musa et al. |
| 2010/0159011 A1 | 6/2010 | Lian et al. |

FOREIGN PATENT DOCUMENTS

| | | |
|---|---|---|
| EP | 0490854 B1 | 9/1996 |
| EP | 1975230 A1 | 1/2008 |
| EP | 2090592 A1 | 8/2009 |
| WO | WO 00/62827 | 10/2000 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/086325 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/003054 A1 | 1/2007 |
| WO | WO 2007/041394 A2 | 4/2007 |
| WO | WO 2007/041451 A2 | 4/2007 |
| WO | WO 2007/047668 A2 | 4/2007 |
| WO | WO 2008/004988 A1 | 1/2008 |
| WO | WO 2008/013618 A1 | 1/2008 |
| WO | WO 2008/031525 A1 | 3/2008 |
| WO | WO 2008/047057 A1 | 4/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |

OTHER PUBLICATIONS

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

R. Riva, et al., "Contribution of "Click Chemisty" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletton and Bertozzi, "A Hydrophilic Azacyclooctyne for Cu-free Click Chemistry", Org. Lett. (2008) 10(14), pp. 3097-3099.

Cazalis, et al., "Bioconjugate Chem.", 15 (2004), pp. 1005-1009.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", J. Chromatogr A., 2008, 1194(2), pp. 165-171.

Hartgerink, et al., "Pepti-damphiphile Nanofibers: A Versatile Scaffold for the Preparation of Self Assembling Materials", PNAS, 2002; 99(2), pp. 5133-5138.

Van Berkel, et al., Cem Bio Chem, 8, (2007), pp. 1504-1508.

Nottelet, et al., Biomaterials, 27, (2006), pp. 4948-4954.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel Domino-click Approach for the Synthesis of Sugar Based Unsymmetrical bis-1,2,3-triazoles", Carbohydrate Research, 343, (2008), 139-144.

Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., "Lipid-Conjugated Oligonucleotides via Click Chemistry" Efficiently Inhibit Hepatitis C Virus Translation, J. med. Chem., 2008, 51(15), pp. 4374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i* + 4 Intramolecular Side-chain to Side-chain Azide-Alkyne 1,3-Dipolar Cycloaddition" J. Org. Chem., 2008, 73 (15), pp. 5663-5674.

Dijk, et al., "Synthesis of Peptide-Based Polymers by Microwave-Assisted Cycloaddition Backbone Polymerization, "Biomacro molecules, 2007, 8(2), pp. 327-330.

Köster, et al.; "Spectroscopic and Electrochemical Studies of Ferroceryl Triazole Amino Acid and Peptide Bioconjugates Synthesized by Click Chemisty", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradeable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

* cited by examiner

US 8,512,728 B2

METHOD OF FORMING A MEDICAL DEVICE ON BIOLOGICAL TISSUE

RELATED APPLICATIONS

This application claims the benefit of U.S. Provisional Patent Application No. 61/154,372 filed Feb. 21, 2009.

BACKGROUND

1. Technical Field

The present disclosure relates to self-assembling adhesive modalities for repair of biological tissues.

2. Related Art

Techniques for repairing damaged or diseased tissue are widespread in medicine. Wound closure devices such as sutures, staples and other repair devices such as mesh or patch reinforcements are frequently used for repair. Surgical adhesives have been used to augment and, in some cases, replace sutures and staples in wound closure. For example, in the case of hernias, techniques involving the use of a mesh or patch to reinforce the abdominal wall are being used. The mesh or patch can generally be held in place by suturing or stapling to the surrounding tissue. Unfortunately, the use of such sutures or staples may increase the patient's discomfort and, in certain instances, there may be a risk of weakening thin or delicate tissue where they are attached. Certain techniques involve placing a mesh or patch against the repair site without suturing or stapling, e.g., allowing the pressure of the peritoneum to hold the patch against the posterior side of the abdominal wall. However, fixation of the mesh or patch is generally preferred in order to avoid folding, shrinkage, and migration of the mesh or patch. Surgical adhesives such as cyanoacrylates and fibrin glues have been used as fixatives in lieu of, or in addition to, suturing or stapling the mesh or patch. However, fibrin adhesives can be difficult to prepare and store. Cyanoacrylates may cause irritation at the point of application and may not provide a sufficient degree of elasticity. In addition, surgical adhesives can tend to form a physical barrier between the item or items being attached to biological tissue, thus interfering with tissue ingrowth into the item when ingrowth is desired. There is a continuing need to generate improvements in tissue repair technology and advance the state of the art.

Click chemistry is a popular term for reliable reactions that make it possible for certain chemical building blocks to "click" together and form an irreversible linkage. See, e.g., US Pub. No. 2005/0222427. Since its recent introduction, click chemistry has been used for ligation in biological and medical technology. In the case of azide-alkyne click chemistry, the reactions may be catalyzed or uncatalyzed. For example, copper-free click chemistry was recently developed by Bertozzi and colleagues using difluorinated cyclooctyne or DIFO, that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, US Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyazacyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions.

SUMMARY

A method for in situ formation of a medical device on biological tissue includes attaching a plurality of reactive members of a primary specific binding pair to a surface of the biological tissue, and providing a plurality of fibers having attached thereto a plurality of complementary reactive members of the primary specific binding pair, wherein upon contact of the reactive members on the surface of the biological tissue with the complimentary reactive members on the fibers, covalent bonds are formed between the reactive members and the complementary reactive members, thus adhering the fibers to the tissue.

DETAILED DESCRIPTION

In accordance with the disclosure herein, polymeric fibers are provided with a plurality of reactive members of one or more specific binding pairs which are attached to the surface of the fiber. When the reactive members of the fibers are contacted with biological tissue containing complementary reactive members of one or more of the specific binding pairs, covalent attachment occurs, thus adhering the fibers to the tissue and optionally to each other. Depending on the nature of the specific binding pairs and the manner and orientation of the reactive members and complementary reactive members on the fibers and the biological tissue, respectively, various fibrous configurations are obtainable which can vary in shape, thickness and patterning. For example, fibrous networks can be formed in situ as matrices, mesh configurations and patches. The fibrous networks assemble in situ and adhere to biological tissue without any barrier between the network and the tissue that would interfere with tissue ingrowth into the network. Indeed, the fibrous network allows beneficial diffusion and exchange of physiological fluids between the site where the network is attached and the surrounding environment. Strength and elasticity of the networks can be varied to suit particular applications based on the nature of the fiber, the number of attachments between the fibers and the tissue, the number of attachments between the fibers themselves and the volume and density of the networks.

Self-assembling fibrous networks adhere to biological tissue in-situ in accordance with the present disclosure. Members of specific binding pairs selectively attach fibers to biological tissue and optionally to each other through covalent bond formation via click chemistry. Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

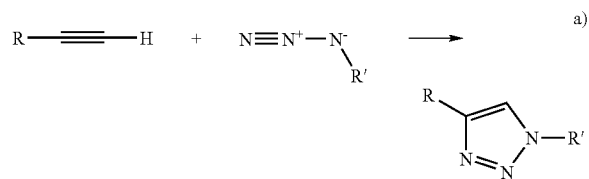

a)

where R is a polymeric backbone and R' is a component of a biologic tissue. Alternatively, R is a component of a biologic tissue and R' is a polymeric backbone.

The Diels-Alder reaction combines a diene (a molecule with two alternating double bonds) and a dienophile (an alkene) to make rings and bicyclic compounds. Examples include:

Dienes

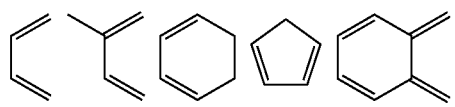

Dienophiles

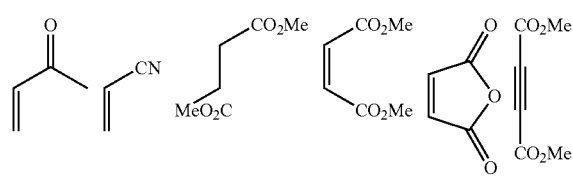

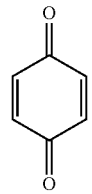

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

Initiation

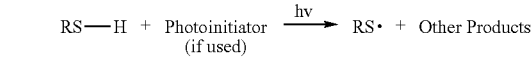

Propagation

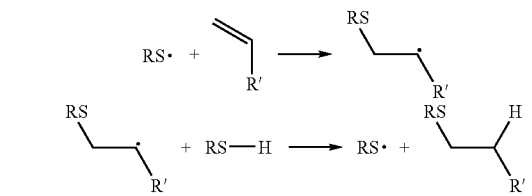

Termination

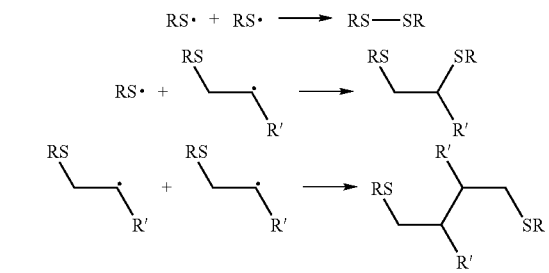

In embodiments, the Huisgen members of a specific binding pair may be either a dipolarophile or a 1,3 dipolar compound depending on which member of the binding pair is applied to the target tissue or the fiber. For example, if a dipolarophile is located on the fiber, the 1,3 dipolar compound can be located on the tissue. If a dipolarophile is located on the tissue, the 1,3 dipolar compound can be located on the fiber. In embodiments, the Diels-Alder members of a specific binding pair may be either a diene and a dienophile depending on which complement is applied to the target tissue or the fiber. For example, if a diene is located on the fiber, the dienophile can be located on the tissue. If a diene is located on the tissue, the dienophile can be located on the fiber. In embodiments, the thiol-ene members of a specific binding pair may be either a thiol and an alkene depending on which complement is applied to the target tissue or the fiber. For example, if a thiol is located on the fiber, the alkene can be located on the tissue. If a thiol is located on the tissue, the alkene can be located on the fiber.

It is contemplated that the respective fibers and tissue can have one or more different members of specific binding pairs attached to increase the permutations available for attaching the fibers to the tissue and for attaching the fibers to each other. For example, a primary specific binding pair may have its members attached to the fibers and the biological tissue, e.g., a plurality of reactive members of the primary specific binding pair are attached to a surface of the biological tissue and a plurality of complementary reactive members of the primary specific binding pair are attached to at least a portion of the length of the fibers. Upon contact of the fibers with the tissue, optionally in the presence of a catalyst such as a metal or ultraviolet radiation depending on the nature of the reaction, the fibers will adhere to the tissue in the location of the reactive members. In embodiments, in addition to the primary specific binding pair, members of an orthogonal specific binding pair can be attached to the fibers in such a manner as to cause the fibers to bond to each other. For example, a plurality of reactive members of the orthogonal specific binding pairs are attached to one group of fibers and a plurality of complementary reactive members of the orthogonal specific binding pair are attached to a second group of fibers and mixed together. After the fibers are applied to the tissue and bonded to the tissue using one reaction scheme for the primary specific binding pair, e.g., a Huisgen reaction, the fibers can be cross-linked by activating the orthogonal specific bind pairs located on the fibers utilizing a different reaction scheme, e.g., thiol-ene. In embodiments, fibers can have both a plurality of reactive members of the primary specific binding pair as well as a plurality of complementary reactive members of the primary specific binding pair attached. Either or both the reactive members of the primary specific binding pair or a plurality of complementary reactive members of the primary specific binding pair are attached to a surface of the biological tissue. The fibers are contacted with the tissue and the reactive groups activated with a catalyst which causes simultaneous bonding of the fibers to the tissue and cross-linking of the fibers to each other. It is contemplated that a second orthogonal binding pair which utilizes the same or different reaction as either or both of the primary specific binding pair or first orthogonal specific binding pair can be incorporated onto the fibers when desired in much the same manner as the first orthogonal specific binding pair, thus causing further selective binding of the fibers to the tissue and/or the fibers to each other.

In embodiments, a primary specific binding pair may have its members attached to a first plurality of fibers and the biological tissue, e.g., a plurality of reactive members of the primary specific binding pair are attached to a surface of the biological tissue and a plurality of complementary reactive members of the primary specific binding pair are attached to at least a portion of the length of the fibers. In addition, a plurality of reactive members of a secondary specific binding pair are also attached to the biological tissue and a second plurality of fibers is provided with a plurality of complementary reactive members of the secondary specific binding pair. Upon contact of the secondary fibers with the tissue, optionally in the presence of a catalyst such as a metal or ultraviolet radiation depending on the nature of the reaction, the secondary fibers will adhere to the tissue in the location of the reactive members. When both the first plurality of fibers and the second plurality of fibers are applied together and allowed to react with the members on the tissues, they will intertwine while binding to the reactive members on the tissue. If the first plurality of fibers is applied separately, e.g., applied first, an initial fibrous network of the first plurality of fibers will assemble. The second plurality of fibers can then be applied and allowed to react, thus causing a second fibrous network to be assembled over the first fibrous network and creating a layered configuration.

In embodiments, the reactive members of the primary specific binding pair can be attached to a surface of the biological tissue in a first geometric pattern. For example, the pattern could be a series of substantially parallel lines or concentric ellipsoids. The pattern can incorporate a series of dots or dashes. It is contemplated that any geometric pattern can be utilized. Similarly, the reactive members of the secondary specific binding pair are attached to a surface of the biological tissue in a second geometric pattern which may or may not overlap the first geometric pattern. For example, the first geometric pattern can be a series of parallel lines and the second geometric pattern can be a series of parallel lines transverse to the first lines, thereby forming a grid. When both the first plurality of fibers and the second plurality of fibers are applied together and allowed to react with the respective members on the tissues, they will assemble into a grid according to their affinities for the respective reactive members. It is contemplated that fibrous networks forming portions of the combined geometric patterns can have different physical properties such as strength, thickness, elasticity depending on whether the fibers are cross-linked in accordance with the disclosure herein, the density of the fibrous network and/or based on the physical and chemical properties of the polymer(s) making up the fibers. Utilizing this feature, one network of defined characteristics can be assembled in one pattern while another network with differing characteristics can be assembled in another pattern. In this manner, the combined fibrous network can be made to have selective qualities such as rigidity in one direction and more flexibility in another, or to incorporate zones having different characteristics. In embodiments, a tertiary specific binding pair can be incorporated onto the fibers and tissue when desired in much the same manner as the secondary specific binding pair. Additional specific binding pairs may also be incorporated. The geometric patterns may be created by painting, spraying, pouring or dripping a mixture containing the reactive members or complementary reactive members onto tissue at a desired location. Any suitable manner of applying a mixture, which can be a solution or suspension is acceptable.

The fibers may be constructed from biocompatible absorbable polymers or biocompatible non-absorbable polymers. Examples of suitable polymers include polycarbonates, polyolefins, polymethacrylates, polystyrenes, polyamides, polyurethanes, polyethylene terephthalate, poly (lactic acid), poly (glycolic acid), poly (hydroxybutyrate), dioxanones (e.g., 1,4-dioxanone), δ-valerolactone, 1,dioxepanones (e.g., 1,4-dioxepan-2-one and 1,5-dioxepan-2-one), poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroiten sulfate, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant. Many of the above described examples of polymers do not contain functional groups in their molecules. In embodiments, the reactive members or complementary reactive members are attached to the fibers by surface modification techniques such as plasma treatment, silane coupling treatment and acid sensitization. Surface activation of the fibers can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2CO_3$, $Ca(OH)_2$ and the weak bases, such as for example $NH_4OH$ and the ammines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a reactive gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the bioabsorbable polymeric substrate. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—$CH_2$—$CH_2$—COOH groups. Suitable surface activation techniques are disclosed in U.S. Pat. No. 6,107,453, the entire disclosure of which is incorporated herein by this reference.

During manufacture of polymers, pendant functional groups can be incorporated into the polymer backbone by, e.g., copolymerization with functionalized monomer such as lactones, cyclic carbonates and morpholine-2,5-diones. The azido group, $N_3$ is a nucleophilic group that will exchange with other nucleophilic groups, e.g., —OH, —$NH_2$ and halogens (Br, Cl, or I). For example, 1,3-dipolar compounds may be conjugated to aliphatic polyesters, by copolymerizing ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with $ZnEt_2$ as a catalyst. See, Shi et al., Biomaterials, 29 (2008)1118-1126. Azide functionalized polystyrene is synthesized using atom transfer radical polymerization and subsequent modification with azidotrimethylsilane and tetrabutylammonium fluoride. See, Dirks, et al., Chem. Comm., (2005) 4172-4174. Azides may be incorporated onto methacrylates, e.g., 3 azidopropyl methacrylate which is copolymerized to a block copolymer.

Diels-Alder functionalities and thiol-ene functionalities are likewise incorporated into polymers herein.

In embodiments, nanofibers are utilized in the self-assembling fibrous networks. Polymeric nanofibers and methods of producing them are known. For example, US Pub No. 2008/0242171, the entire disclosure of which is incorporated herein by this reference, describes production of nanofibers produce polymeric nanofibers that have mean fiber diameters of less than about 1,000 nm by melt spinning. Prior to or after formation of polymeric nanofibers, the polymers which are formed into the nanofibers are functionalized as described above. Peptide-amphiphile nanofibers may be utilized herein. Peptide amphiphile compounds, compositions and methods for self-assembly or nanofibrous network formation under neutral or physiological conditions are described, e.g., in U.S. Pat. No. 7,371,719, the entire disclosure of which is incorporated herein by this reference. In embodiments, a functionalized nanofiber can be prepared by combining plurality of amphiphilic compounds with a solvent to form a self-assembling composition. The amphiphilic compounds include a hydrophilic portion and a hydrophobic portion with the hydrophilic portion functionalized with one or more first reactive members and one or more second reactive members, the second reactive member being complementary to the first reactive member. When added to a hydrophilic solvent, the amphiphilic compounds self-assemble to form a linear micelle or nanofiber, with the hydrophilic portions aligned along the exterior of the nanofiber and the hydrophobic portions gathered near the interior of the nanofiber. The complementary first and second reactive members of the amphiphilic compounds provide for the covalent attachment of adjacent amphiphilic compounds when a first reactive member of one amphiphilic compound reacts with to a second reactive member of another amphiphilic compound to provide radial cross-linking as well as longitudinal cross-linking along the length of the nanofiber to stabilize the self assembled structure. In addition to the first and second reactive members, the hydrophilic portion of the amphiphilic compound also includes a terminal reactive member of a specific binding pair that provides reactive sites at the surface of the nanofiber. The self assembled structure having an activated surface can be attached to biological tissue in accordance with methods described in the present disclosure.

Biological tissue is provided with reactive members of a specific binding pair by conjugation to various components of tissue such as proteins, lipids, oligosaccharides, oligonucleotides, glycans, including glycosaminoglycans. In one embodiment, the reactive members or complementary reactive members are attached directly to components of the tissue. In another embodiment, the reactive members or complementary reactive members are attached to components of the tissue via a linker. In either case, situating the reactive members or complementary reactive members on the tissue can be accomplished by suspending the reactive members or complementary reactive members in a solution or suspension and applying the solution or suspension to the tissue such that the reactive member binds to a target. The solution or suspension may be poured, sprayed or painted onto the tissue, whereupon the reactive members or complementary reactive members are incorporated into the tissue.

1,3-Dipolar compounds can be incorporated into proteins, lipids, oligosaccharides, oligonucleotides and glycans using, e.g., metabolic machinery, covalent inhibitors and enzymatic transfers. For example, an azido group, $N_3$, can be applied at the N-terminus of proteins or peptides using azidoacetyl chloride. See, e.g., Haridas, et al., Tetrahedron Letters 48 (2007) 4719-4722. The azido group is a nucleophilic group that will exchange with other nucleophilic groups, e.g., —OH, —NH$_2$ and halogens (Br, Cl, or I). NaN$_3$ is an azidizing agent which is capable of aziding proteins by simply contacting the proteins with a 10 times molar excess of NaN$_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azidotagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive group. Reactive groups (as opposed to reactive members herein) are those to which an activated PEG molecule may be bound (e.g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate), in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with propargylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16 carbon alkynyl-dimethylphosphonate. See, e.g., Raghavan et al., Bioorg. Med. Chem. Lett., 18 (2008) 5982-5986. As above, PEGylation may be used for adding dipolarophile groups to to peptides and proteins and is suitable for use herein. Diels-Alder functionalities and thiol-ene functionalities are likewise attached to proteins, lipids, oligosaccharides, oligonucleotides and glycans.

The reactive members or complementary reactive members may be also attached to biological tissue via a linker. In certain embodiments, the linker is or includes a ligand which bears a reactive member. The ligand binds to a desired target on the tissue and thus provides a vehicle for transporting and indirectly binding the reactive member to the tissue. The ligand herein is any molecule or combination of molecules which demonstrates an affinity for a target. Examples of ligands include nucleic acid probes, antibodies, hapten conjugates, and cell adhesion peptides such as RGD. The mechanisms involved in obtaining and using such ligands are well-known. In embodiments, reactive members or complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to a reactive member are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides) are conjugated or linked to reactive members or complementary reactive members in the manners described above. In addition, reactive members or complementary reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the reactive members or complementary reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl)cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and $N,N^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of reactive members to the fibers functionalizes the fibers such that upon exposure to their complementary reactive members which are situated on tissue, they are activated and form a covalent bond, thus adhering the fibers to the tissue. In one embodiment, a linker between the product of the reactive members or complementary reactive members and the biological tissue is degradable by, e.g., hydrolysis or enzymatic action. In this manner, the self assembled fibrous network can be removable after a period of time. The degradable linkage may be, e.g., chelates or chemically or enzymatically hydrolyzable or absorbable. Illustrative chemically hydrolyzable degradable linkages include polymers, copolymers and oligomers of glycolide, dl-lactide, l-lactide, caprolactone, dioxanone, and tritnethylene carbonate. Illustrative enzymatically hydrolyzable biodegradable linkages include peptidic linkages cleavable by metalloproteinases and collagenases. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The fibers may be extruded to various diameters and cut to desired lengths, packaged in single or dual pouches and sterilized by gamma or beta irradiation at 25-35 Kgy or by ethylene oxide. The ligand solution could be sterilized by the previous cited method or by filtration in sterile conditions on 0.22 um filter.

A kit for a forming self assembling fibrous networks herein includes a plurality of fibers which have a plurality of reactive members of a specific binding pair attached to a surface of the fibers and a container which optionally functions as an applicator and is adapted to contain a mixture including complementary reactive members of the specific binding pair, the complementary reactive members having a functionality that will adhere them to biological tissue upon contact. The kit may optionally include a container which contains a catalyst for causing the reactive members of a specific binding pair to bind with the complementary reactive members of the specific binding pair. The catalyst may be a metal. In embodiments, the kit contains a generator of microwave or ultraviolet radiation.

It should be understood that variations can be made to the above embodiments that are with the purview of ordinary skill in the art. For example, other click chemistry reactions are suitable for use herein, e.g., Staudinger reaction of phosphines with alkyl azides. It is contemplated that the above-described cross-linkers may be applied to polymers which make up the fibers to bind reactive members or complementary reactive members thereto. Additional binding pairs may be incorporated into the networks and tissue. Medicinal agents such as drugs, growth factors, radiologic dyes can be incorporated into the fibers and networks according to known techniques. Accordingly, those skilled in the art can envision modifications which are included within the scope of the claimed invention that are not expressly set forth herein.

What is claimed is:

1. A method of forming a medical device on biological tissue comprising:
attaching a plurality of reactive members of a primary specific binding pair to a surface of the biological tissue;
providing a plurality of fibers having attached thereto a plurality of complementary reactive members of the primary specific binding pair, and a plurality of reactive members and complementary reactive members of an orthogonal specific binding pair, wherein upon contact of the reactive members of the primary specific binding pair on the surface of the biological tissue with the complimentary reactive members of the primary specific binding pair on the fibers, covalent bonds are formed via click chemistry between the reactive members and the complementary reactive members of the primary specific binding pair, adhering the fibers to the biological tissue, and, wherein upon contact of the reactive members of the orthogonal specific binding pair on the fibers with the complimentary reactive members of the orthogonal specific binding pair on the fibers, covalent bonds are formed via click chemistry between the reactive members and the complementary reactive members of the orthogonal specific binding pair, adhering the fibers to each other.

2. The method of forming a medical device on biological tissue according to claim 1 wherein the plurality of fibers further comprise reactive members and the complementary reactive members of a second orthogonal specific binding pair capable of causing the plurality of fibers to bind to each other.

3. The method of forming a medical device on biological tissue according to claim 1 wherein the reactive members and the complementary reactive members of the primary specific binding pair bind to one another to form covalent bonds via a reaction selected from the group consisting of Huisgen cycloaddition reaction, a Diels-Alder reaction and a thiol-ene reaction.

4. The method of forming a medical device on biological tissue according to claim 3 wherein the reactive members and the complementary reactive members of the primary specific binding pair are alkynes and azides.

5. The method of forming a medical device on biological tissue according to claim 2 wherein the plurality of fibers comprises a first group of the plurality of fibers with a plurality of reactive members of the second orthogonal specific binding pair and a second group of the plurality of fibers with a plurality of complementary reactive members of the second orthogonal specific binding pair, wherein upon contact of the reactive members of the second orthogonal specific binding pair with the complimentary reactive members of the second orthogonal specific binding pair, covalent bonds are formed between the reactive members and the complementary reactive members of the second orthogonal specific binding pair, adhering the first and second group of fibers to each other.

6. The method of forming a medical device on biological tissue according to claim 5 wherein the reactive members and the complementary reactive members of the second orthogonal specific binding pair bind to one another to form covalent bonds via a reaction selected from the group consisting of Huisgen cycloaddition reaction, a Diels-Alder reaction and a thiol-ene reaction.

7. The method of forming a medical device on biological tissue according to claim 6 wherein the reactive members and the complementary reactive members of the second orthogonal specific binding pair bind to one another to form covalent bonds via a reaction which is different than the reaction of the orthogonal specific binding pair.

8. The method of forming a medical device on biological tissue according to claim 6 wherein the reactive members and the complementary reactive members of the second orthogonal specific binding pair bind to one another to form covalent bonds via a reaction which is different than the reaction of the primary specific binding pair.

9. The method of forming a medical device on biological tissue according to claim 1 wherein reactive members of the primary specific binding pair are attached to the tissue to form covalent bonds via attachment to a moiety selected from the group consisting of an N-terminus of a protein of the tissue, a C-terminus of a protein of the tissue, an oligosaccharide, a lipid, a glycan and an oligonucleotide.

10. The method of forming a medical device on biological tissue according to claim 1 wherein reactive members of the primary specific binding pair are attached to the biological tissue by applying a mixture or an aerosol containing the reactive members to the biological tissue, the reactive members being conjugated to a linker adapted to link the reactive members to the biological tissue.

11. The method of forming a medical device on biological tissue according to claim 10 wherein the reactive members of the primary specific binding pair are attached to the biological tissue via an RGD linker.

12. The method of forming a medical device on biological tissue according to claim 10 wherein the reactive members of the primary specific binding pair are attached to the biological tissue via a ligand-receptor linkage.

13. The method of forming a medical device on biological tissue according to claim 12 wherein the reactive members of the primary specific binding pair are conjugated to a linker selected from the group consisting of antibody, Fab, F(ab')$_2$, Fv, single chain antibody (SCA) and single complementary-determining region (CDR).

14. The method of forming a medical device on biological tissue according to claim 10 wherein the linker is degraded by hydrolysis or enzymatic action.

15. The method of forming a medical device on biological tissue according to claim 12 wherein the ligand binds to a receptor selected from the group consisting of peptides, oligosaccharides, oligonucleotides, glycans and lipids.

16. The method of forming a medical device on biological tissue according to claim 1 wherein the fibers are nanofibers.

17. The method of forming a medical device on biological tissue according to claim 1 wherein the reactive members of the primary specific binding pair are applied to the surface of the biological tissue in a predetermined geometric pattern.

18. The method of forming a medical device on biological tissue according to claim 17 wherein the predetermined geometric pattern defines a mesh.

19. The method of forming a medical device on biological tissue according to claim 1 wherein the plurality of fibers are made of a polymer selected from the group consisting of polycarbonates, polyolefins, polymethacrylates, polystyrenes, polyamides, polyurethanes, polyethylene terephthalate, poly (lactic acid), poly (glycolic acid), poly (hydroxybutyrate), poly (phosphazine), polyesters, polyethylene glycol, polyethylene oxides, polyacrylamides, fluoropolymers, vinyl polymers, silk, collagen, alginate, chitin, chitosan, hyaluronic acid, chondroiten sulfate, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyoxaesters, polyorthoesters, polyphosphazenes, polypeptides and copolymers, block copolymers, homopolymers, blends and combinations thereof.

20. The method of forming a medical device on biological tissue according to claim 1 wherein the fibers adhere to the biological tissue in the form of a medical device selected from the group consisting of a mesh, patch, adhesion barrier and hemostat.

21. A method of forming a medical device on biological tissue comprising:
attaching a plurality of reactive members of a primary specific binding pair to a surface of the biological tissue;
providing a first plurality of fibers having attached thereto a plurality of complementary reactive members of the primary specific binding pair, and a plurality of reactive members of an orthogonal specific binding pair, wherein upon contact of the reactive members of the primary specific binding pair on the surface of the biological tissue with the complimentary reactive members of the primary specific binding pair on the first plurality of fibers, covalent bonds are formed via click chemistry between the reactive members and the complementary reactive members of the primary specific binding pair, adhering the first plurality of fibers to the biological tissue; and,
providing a second plurality of fibers having attached thereto a plurality of complementary reactive members of the primary specific binding pair, and a plurality of complementary reactive members of the orthogonal specific binding pair, wherein upon contact of the reactive members of the primary specific binding pair on the surface of the biological tissue with the complimentary reactive members of the primary specific binding pair on the second plurality of fibers, covalent bonds are formed via click chemistry between the reactive members and the complementary reactive members of the primary specific binding pair, adhering the second plurality of fibers to the biological tissue, and, wherein upon contact of the reactive members of the orthogonal specific binding pair on the first plurality of fibers with the complimentary reactive members of the orthogonal specific binding pair on the second plurality of the fibers, covalent bonds are formed via click chemistry between the reactive members and the complementary reactive members of the orthogonal specific binding pair, adhering the first and second plurality of fibers to each other.

22. The method of forming a medical device on biological tissue according to claim 21 wherein the reactive members and the complementary reactive members of the orthogonal specific binding pair bind to one another to form covalent bonds via a reaction selected from the group consisting of Huisgen cycloaddition reaction, a Diels-Alder reaction and a thiol-ene reaction.

23. The method of forming a medical device on biological tissue according to claim 22 wherein the reactive members and the complementary reactive members of the orthogonal specific binding pair bind to one another to form covalent bonds via a reaction which is different than the reaction of the primary specific binding pair.

24. The method of forming a medical device on biological tissue according to claim 21 wherein the reactive members and the complementary reactive members of the primary specific binding pair bind to one another to form covalent bonds via a reaction catalyzed by copper to activate an alkyne and an azide for [3+2] cycloaddition.

25. The method of forming a medical device on biological tissue according to claim 21 wherein the reactive members and the complementary reactive members of the primary specific binding pair bind to one another to form covalent bonds via a reaction comprising a cyclooctyne reagent and an azide for [3+2] cycloaddition.

26. A method of forming a medical device on biological tissue comprising:
    attaching a plurality of reactive members of a primary specific binding pair and a plurality of reactive members of a secondary specific binding pair to the surface of the biological tissue;
    providing a first plurality of fibers having attached thereto a plurality of complementary reactive members of the primary specific binding pair, wherein upon contact of the reactive members of the primary specific binding pair on the surface of the biological tissue with the complimentary reactive members of the primary specific binding pair on the first plurality of fibers, covalent bonds are formed via click chemistry between the reactive members and the complementary reactive members of the primary specific binding pair, adhering the first plurality of fibers to the biological tissue; and
    providing a second plurality of fibers having attached thereto a plurality of complementary reactive members of the secondary specific binding pair, wherein upon contact of the reactive members of the secondary specific binding pair on the surface of the biological tissue with the complimentary reactive members of the secondary specific binding pair on the second plurality of fibers, covalent bonds are formed via click chemistry between the reactive members and the complementary reactive members of the secondary specific binding pair, adhering the second plurality of fibers to the biological tissue.

27. The method of forming a medical device on biological tissue according to claim 26 wherein the first plurality of fibers further comprises a plurality of reactive members of an orthogonal specific binding pair, and the second plurality of fibers further comprises a plurality of complementary reactive members of the orthogonal specific binding pair, wherein upon contact of the reactive members of the orthogonal specific binding pair on the first plurality of fibers with the complimentary reactive members of the orthogonal specific binding pair on the second plurality of the fibers, covalent bonds are formed via click chemistry between the reactive members and the complementary reactive members of the orthogonal specific binding pair, adhering the first and second plurality of fibers to each other.

28. The method of forming a medical device on biological tissue according to claim 26 wherein the first plurality of fibers are applied to the surface of the biological tissue in a first geometric pattern and the second plurality of fibers are applied to the surface of the biological tissue in a second geometric pattern.

29. The method of forming a medical device on biological tissue according to claim 28 wherein the first geometric pattern and the second geometric pattern intersect.

30. The method of forming a medical device on biological tissue according to claim 26 further comprising:
    attaching a plurality reactive members of a tertiary specific binding pair to the surface of the biological tissue; and
    providing a third plurality of fibers having attached thereto a plurality of complementary reactive members of the tertiary specific binding pair, wherein upon contact of the reactive members of the tertiary specific binding pair on the surface of the biological tissue with the complimentary reactive members of the tertiary specific binding pair on the third plurality of fibers, covalent bonds are formed between the reactive members and the complementary reactive members of the tertiary specific binding pair, adhering the third plurality of fibers to the biological tissue.

31. The method of forming a medical device on biological tissue according to claim 30 wherein the third plurality of fibers intertwines with the first plurality of fibers and the second plurality of fibers.

32. The method of forming a medical device on biological tissue according to claim 30 wherein the first plurality of fibers are applied to the surface of the biological tissue in a first geometric pattern and the third plurality of fibers are applied to the surface of the biological tissue in a different geometric pattern.

33. The method of forming a medical device on biological tissue according to claim 32 wherein the first geometric pattern and the different geometric pattern intersect.

* * * * *